United States Patent [19]

Saunders et al.

[11] 4,141,995

[45] Feb. 27, 1979

[54] KETONE DERIVATIVES

[75] Inventors: John C. Saunders, Maidenhead; William R. N. Williamson, Slough, both of England

[73] Assignee: Lilly Industries Limited, London, England

[21] Appl. No.: 830,259

[22] Filed: Sep. 2, 1977

Related U.S. Application Data

[63] Continuation of Ser. No. 676,823, Apr. 14, 1976, abandoned.

[30] Foreign Application Priority Data

Apr. 17, 1975 [GB] United Kingdom ............... 15805/75

[51] Int. Cl.$^2$ .......................... C07C 49/82; A01N 9/24
[52] U.S. Cl. ..................................... 424/331; 260/591
[58] Field of Search ........................ 260/591; 424/331

[56] References Cited

U.S. PATENT DOCUMENTS

| | | | |
|---|---|---|---|
| 3,120,564 | 2/1964 | Milionis et al. | 260/591 |
| 3,222,359 | 12/1965 | Reeder et al. | 260/591 |
| 3,924,002 | 12/1975 | Duennenberger et al. | 260/591 |

OTHER PUBLICATIONS

Physicians Desk Reference, pp. 760–761 (1974).

*Primary Examiner*—James O. Thomas, Jr.
*Assistant Examiner*—James H. Reamer
*Attorney, Agent, or Firm*—James L. Rowe; Everet F. Smith

[57] ABSTRACT o-Hydroxybenzophenones and derivatives thereof are described together with a process for their production. The compounds have anti-allergy activity and are characterized by the presence of an alkyl substituent on the hydroxyphenyl ring.

3 Claims, No Drawings

KETONE DERIVATIVES

This is a continuation of application Ser. No. 676,823 filed Apr. 14, 1976 now abandoned.

BACKGROUND OF THE INVENTION

There is a wealth of literature concerning the benzophenones, their preparation and their uses. However, it has not heretofore been appreciated that o-hydroxybenzophenones, and derivatives thereof, can be used in the treatment of allergic conditions.

SUMMARY OF THE INVENTION

This invention relates to a class of novel benzophenones, and derivatives thereof, to methods of preparing such derivatives, to pharmaceutical formulations and to methods of treating allergic conditions involving use of o-hydroxybenzophenones.

According to the present invention, therefore, there is provided a pharmaceutical formulation containing an active ingredient in association with a pharmaceutically acceptable carrier therefor, said active ingredient being a compound of the formula:

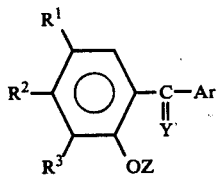

(I)

wherein $R^2$ is hydrogen or ethyl, $R^1$ and $R^3$ represent hydrogen, methyl or ethyl, at least one of $R^1$, $R^2$ and $R^3$ not being hydrogen; Ar is a phenyl group optionally substituted by from one to three groups selected from chlorine, fluorine, methyl, carboxy, $COOR^5$ and trifluoromethyl; Z is hydrogen or $COR^5$; and Y is O, NOH or $NOCOR^5$, $R^5$ being $C_{1-4}$ alkyl or phenyl, provided that
  i. when Ar is 4-chlorophenyl, Y and Z are as defined above and $R^1$ and $R^2$ are hydrogen, $R^3$ is methyl;
  ii. when Ar is unsubstituted phenyl, Z is as defined above, $R^1$ and $R^2$ are hydrogen and $R^3$ is ethyl, Y can only be O;
  iii. when $R^1$ is ethyl, $R^2$ and $R^3$ are hydrogen and Y and Z are as defined above, Ar cannot be 2,4- or 3,4-dichlorophenyl, 2- or 3-chlorophenyl or 4-fluorophenyl; and
  iv. when Ar is unsubstituted phenyl, Y and Z are as defined above, and $R^1$ and $R^2$ are hydrogen, $R^3$ is ethyl;

In a further aspect of the invention, there is provided a method of treating a mammal suffering from an allergic condition, and particularly a method of treating immediate hypersensitivity diseases such as asthma in mammals, including humans, which comprises administering to said mammal an anti-allergically effective dose of a compound of formula (I) as defined above.

In the formulation and method aspects of the present invention, a preferred sub-genus of the compounds of formula (I) are those wherein $R^1$, $R^2$ and $R^3$ are as defined above, Ar is a phenyl group optionally substituted by from one to three groups selected from chlorine, fluorine or methyl, Z is hydrogen or $COR^5$ and Y is O, NOH or $NOCOR^5$, $R^5$ being as defined above. Most preferred are those compounds of formula (I) wherein one of $R^1$, $R^2$ and $R^3$ is ethyl and the others are hydrogen; Ar is phenyl, 4-chlorophenyl, 4-fluorophenyl or 4-methylphenyl; Z is hydrogen; and Y is O and, within the latter group, a preferred sub-class are those compounds of formula (I) wherein Z is hydrogen; Y is O and either
  i. $R^1$ is ethyl, $R^2$ and $R^3$ are hydrogen and Ar is 4-chlorophenyl;
  ii. $R^3$ is ethyl, $R^1$ and $R^2$ are hydrogen and Ar is 2,4-dichlorophenyl; or
  iii. $R^2$ is ethyl, $R^1$ and $R^3$ are hydrogen and Ar is 3- or 4-fluorophenyl.

As well as the above particularly preferred groups of compounds of the present invention for use in therapeutic processes and formulations, it has been found that the compounds of formula (I) likely to possess the most useful therapeutic index; i.e. combination of high efficacy and lack of toxicity, are those having one or more of the following features:
  a. Z is hydrogen.
  b. Y is O.
  c. one of $R^1$, $R^2$ and $R^3$ is ethyl, the other $R^1$, $R^2$, $R^3$ substituents being hydrogen.
  d. $R^1$ is ethyl when $R^2$ and $R^3$ are hydrogen.
  e. Ar is a 4-chlorophenyl group.
  f. Ar is a 4-fluorophenyl group.
  g. Ar is unsubstituted phenyl.

A number of the most useful compounds of formula (I) are novel and form a part of this invention. Such novel compounds are those of formula (I) wherein $R^1$, $R^2$ and $R^3$ represent hydrogen or ethyl, at least one being ethyl, Ar is a phenyl group substituted by from one to three groups selected from chlorine, fluorine, methyl, carboxy, $COOR^5$ and trifluoromethyl; Z is hydrogen or $COR^5$; and Y is O, NOH or $NOCOR^5$, $R^5$ being $C_{1-4}$ alkyl or phenyl, provided that,
  when $R^1$ is ethyl, $R^2$ and $R^3$ are hydrogen and Y and Z are as defined above, Ar is not 2,4- or 3,4-dichlorophenyl, 2- or 3-chlorophenyl or 4-fluorophenyl.

A preferred group of novel compounds are those wherein Ar is a phenyl group substituted by from one to three groups selected from chlorine, fluorine or methyl. Particularly useful activity is found in those compounds wherein one of $R^1$, $R^2$ and $R^3$ is ethyl and the others are hydrogen, Ar is 4-chlorophenyl, 4-fluorophenyl or 4-methylphenyl, Z is hydrogen, and Y is O, and especially in these compounds wherein Z is hydrogen, Y is O and either
  i. $R^1$ is ethyl, $R^2$ and $R^3$ are hydrogen and Ar is 4-chlorophenyl;
  ii. $R^3$ is ethyl, $R^1$ and $R^2$ are hydrogen and Ar is 2,4-dichlorophenyl; or
  iii. $R^2$ is ethyl, $R^1$ and $R^3$ are hydrogen and Ar is 3- or 4-fluorophenyl.

Compounds in which Y is NOH or $NOCOR_5$ can exist in both syn and anti forms and it is to be understood that both of these isomers, and mixtures thereof, are included within the scope of the invention.

The preferred novel compound of the invention is 4'-chloro-5-ethyl-2-hydroxybenzophenone.

The present invention also provides a process for preparing the aforementioned novel compounds of formula (I) characterised in that a carboxylic acid of the formula A-COOH or a derivative thereof wherein A is either Ar-or the group.

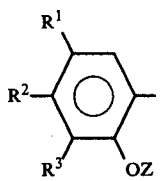

wherein Ar, $R_1$, $R_2$, $R_3$ and Z are defined as above is reacted under Friedel-Crafts' acylating conditions with a substituted benzene of formula B-H wherein B is selected from the same groups as A but is different therefrom to produce a compound of formula (I) in which Y is O and thereafter, where desired, the resultant product is reacted with hydroxylamine in the presence of a base to produce the corresponding oxime in which Y is NOH, a compound in which Z is $COR^5$ and/or Y is $NOCOR^5$ being then obtained by acylation of the aforementioned compounds in which Z is hydrogen and/or Y is NOH.

Illustrative of a Friedel-Crafts' acylation as described above is the reaction between a compound of formula ArCOX and a compound of formula:

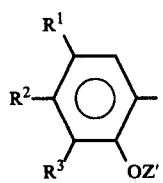

Z' being hydrogen or a protecting group such as methyl.

The reaction may be represented by the following reaction scheme:

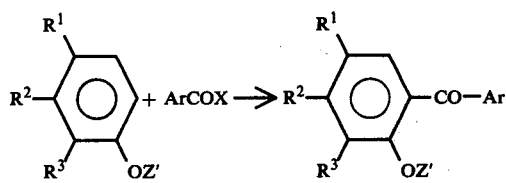

wherein X is a halogen atom or hydroxyl.

When X is halogen, the reaction may be carried out using a Lewis acid such as an aluminium halide (e.g. the chloride) as catalyst in a suitable inert solvent such as 1,1,2,2-tetrachloroethane or carbon disulphide.

When X is hydroxyl, boron trifluoride or $(CF_3CO)_2O$ are preferred catalysts, used with or without a suitable solvent.

If Z' is a protecting group, it may be removed in situ or subsequently, should it be desired to form a compound of formula (I) in which Z' is hydrogen.

Using standard dealkylation (ether splitting) procedures reduction of unwanted isomer(s) can be achieved by suitable choice of reaction conditions, temperature control being especially important. Ideally the reaction temperature is from 20° C. to the reflux temperature and preferably from 80° C. up to the reflux temperature of the reaction mixture.

Similarly, the benzophenones useful in this invention can be prepared by the following reaction scheme:

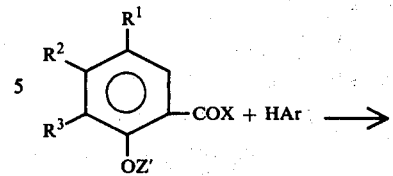

similar reaction conditions being applicable.

In the case of the reaction with a compound of the formula ArCOX, an initial reaction product (A) below may be obtained and isolated. This may be subjected to a Fries rearrangement using similar catalytic conditions:

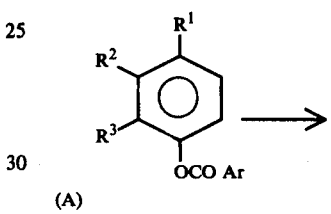

(A)

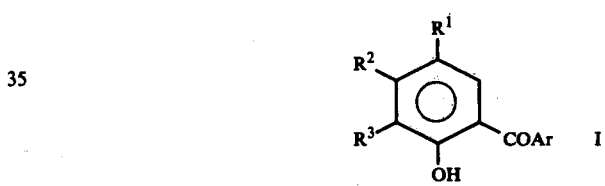

as those described above, for example using aluminium chloride.

A further example of the acylation involving a derivative of A-COOH is the use of the compound Ar-CN as acylating agent. This modified process is known as the Houben-Hoesch Reaction which proceeds as shown below:

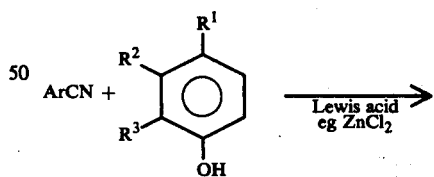

Where an ether-protected hydroxy group Z' is used in the foregoing reactions it may be converted to the desired hydroxy group by cleavage with, for example, HBr, $BF_3$, $AlCl_3$ or HI.

As outlined above, preparation of ketonic derivatives such as the oxime can be effected by combining a solution of the ketone, for example, an aqueous or alcoholic solution, with a derivative, preferably the hydrochloride, of hydroxylamine in the presence of a base, for instance sodium or potassium hydroxide.

Also, as stated above, preparation of the acyl derivatives of the o-hydroxy or oxime groups can be carried out by a variety of methods, for example, by treating the o-hydroxybenzophenone or oxime in a basic solution (e.g. pyridine or an aqueous solution of a group IA hydroxide such as sodium or potassium hydroxide) with an acid anhydride or halide (preferably the chloride) or with a solution of the acylating acid in the presence of the acid anhydride with a trace of catalyst (e.g. perchloric acid - 70%), or by refluxing the o-hydroxybenzophenone or oxime with the acrylating acid.

The o-hydroxybenzophenones and derivatives thereof of the present invention have been shown to possess activity in one or more of the four tests regularly used to detect anti-allergy activity. Two of said tests are in vitro tests - the guinea pig and human chopped lung tests - and involve the direct measurement of the mediators, histamine and slow reacting substance in anaphylaxis (SRS-A), shown to be released by asthmatic human lung. For compounds of the type comprising the present invention, a compound is considered to be active if at least 30% inhibition of SRA-A release in the guinea pig chopped lung test is achieved at a dose of 10 $\mu$g/ml or less. Depending on absorption, distribution and metabolism of the drug under test, activity in the chopped lung test at this level indicates in vivo dosage ranging from 0.5 to about 100 mg/Kg orally.

The other two tests are in vivo tests - the Herxheimer and rat peritoneal anaphylaxis - and reflect oral activity in two different species. In the Herxheimer test, sensitised guinea pigs are protected against the bronchospasm induced by an aerosol of antigen whilst, in the rat peritoneal anaphylaxis test, the SRS-A released on challenge is measured directly. Where an active compound is tested in these in vivo tests, activity at doses of 300 mg/Kg or less is normally achieved.

The compounds of the present invention display activity in one or more of the foregoing tests (the broadest spectrum compounds being those which display anti-allergy activity in all four tests) and are therefore useful in the prophylactic and therapeutic treatment of immediate hypersensitivity diseases including asthma and in the alleviation of status asthmaticus. In certain cases the compounds have been found to be useful in diseases in which excessive amounts of prostaglandins are released, some of the compounds are useful as respiratory stimulants. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I).

As indicated by the tests referred to above, dosages of from 0.5 to 300 mg/kg per day, preferably 0.5 to 20 mg/kg, of active ingredient may be administered. It will however readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) associated with a pharmaceutically acceptable carrier therefor, i.e. mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbital, mannitol, propylene glycol, liquid paraffin, white soft paraffin, kaolin, fumed silicon dioxide, microcrystalline cellulose, calcium silicate, silica, polyvinylpyrrolidine, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoro methane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The following Examples further illustrate the invention:

EXAMPLE 1

2-Hydroxy-5-Methyl-4'-Chlorobenzophenone Oxime (syn. and anti).

(a) 2-Hydroxy-5-methyl-4'chlorobenzophenone (13.5 g, 0.055 moles) was stirred with a solution of potassium hydroxide (44 g.) in water (150 ml.) and then hydroxylamine hydrochloride (17.4 g, 0.25 mole) was added with ice cooling. After stirring overnight at room temperature 100 ml. of water was added and the mixture was acidified with 5N-hydrochloric acid to give an off-white precipitate which was filtered, washed and dried (14.7 g).

Recrystallisation of the product from benzene gave 2-hydroxy-5-methyl-4'-chlorobenzophenone oxime (7 g.) m.p. 163° C. (This was the stereoisomer in which the oxime -OH group and the 4'-chlorophenyl group were in the syn position relative to each other).

(b) The above procedure was repeated this time using 192 g (0.78 mole) of the benzophenone used in (a). The benzene solution deposited a second and third crop of crystals. The second crop (31.5 g) was a mixture of the two forms of the oxime whereas the third crop (1.9 g) was the stereoisomer in which the oxime hydroxyl group and the 4'-chlorophenyl group were in the anti-position relative to each other. (m.p. of product was 145°–7° C.).

The C,H,N,Cl microanalysis for each isomer was satisfactory.

(c) 4'-Chloro-2-hydroxy-5-methyl-benzophenone-oxime diacetate.

The oxime produced in (a) above (26.2 g) was dissolved in warm acetic anhydride (50 ml.), and on cooling a solid separated. This was filtered off and the filtrate evaporated to dryness, leaving a residue which was crystallised from ethanol to give the diacetate as the second crop. (m.p. 136° C.)

EXAMPLE 2

4'-Chloro-5-ethyl-2-hydroxybenzophenone

Aluminium chloride (267 g) was added in portions over 30 minutes to a stirred solution of 4-ethylphenol (122.1 g.) and 4-chlorobenzoyl chloride (140 ml.) in dry 1,1,2,2-tetrachloroethane (800 ml.). The mixture was heated at 105° C. for 22 hours with stirring, and on cooling a mixture of ice (600 g) and concentrated hydrochloric acid was added slowly. A vigorous reaction occurred and some material was lost. The remaining material was separated, the aqueous fraction extracted twice with chloroform (200 ml.), and the combined organic layers evaporated to a dark oil which was distilled in vacuo giving two main fractions: B (17.4 g) 150°–160° C. at 0.3 mmHg; C (110.8 g) 160°–168° C. at 0.3 mmHg. The title compound was crystallised by cooling to −20° C. and recrystallised from n-hexane at 0° C. to give a yellow crystalline solid m.p. 35°–8° C.

Microanalysis: $C_{15}H_{13}ClO_2$ requires 69.1% C, 5.0% H, 13.6% Cl; found 69.0% C, 5.0% H, 13.9% Cl.

EXAMPLE 3

4'-Chloro-5-ethyl-2-hydroxybenzophenone-oxime

4'-Chloro-5-ethyl-2-hydroxybenzophenone (65.2 g) and potassium hydroxide (170 g) in water (700 ml) and ethanol (150 ml.) were treated with hydroxylamine hydrochloride (70.0 g), with cooling, and the resulting mixture was stirred for 18 hours at ambient temperature. Dissolution occurred during this time. The solution was acidified with 5N-hydrochloric acid and then extracted with ether (3 × 200 ml.). The combined ether solutions were washed with 10% aqueous sodium carbonate solution (2 × 200 ml.) and evaporated to dryness to give an off-white solid. This solid was recrystallised from 40% benzene/60°–80° C. petrol ether to give a white crystalline solid (29.9 g), second crop (14.5 g) m.p. 117° C.

Microanalysis: $C_{15}H_{14}ClNO_2$ requires 65.3% C, 5.1% H, 5.1% N, 12.9% Cl; found 65.3% C, 4.9% H, 5.1% N, 12.9% Cl.

(Stereoisomer as in Example 1(a)).

EXAMPLE 4

2-Hydroxy-3-methyl-4'-chlorobenzophenone

Chlorobenzene (78.79 g, 71.6 ml; 0.7 mole) and AlCl₃ (14 g, 0.105 mole) were mixed, stirred and treated with a solution of 2-hydroxy-3-methylbenzoic acid chloride (12 g, 0.07 mole) in chlorobenzene (20 ml). The mixture was stirred and heated at 100° C. overnight. The cooled mixture was added to conc. HCl (10 ml) and ice, extracted with ether, and ether washed with saturated sodium bicarbonate solution, dried (Na₂SO₄), filtered and the filtrate distilled, to give (after removal of the ether), a main fraction 2-hydroxy-3-methyl-4'-chlorobenzophenone, b.p. 148°–152° C./0.5 mm (8.18 g), which solidified to yellow microplates, m.p. 55°–58° C.

found: C. 68.23; H. 4.71; Cl. 14.61; $C_{14}H_{11}ClO_2$ requires: C. 68.16; H. 4.49; Cl. 14.37%

EXAMPLE 5

4-Ethyl-4'-fluoro-2-hydroxybenzophenone

3-Ethylphenol (24.4 g) and 4-fluorobenzoyl chloride (34.9 g) were reacted together as in Example 2 giving three main fractions: B (11.4 g) 126°–129° C. at 0.07 mmHg; C (7.9 g), 129°–132° C. at 0.06 mmHg; D (5.9 g), 132°–150° C. at 0.06 mmHg, all containing ∼ 80% of the required isomer. B (4.0 g) was separated by preparative thin layer chromatography to give the title compound (2.6 g), m.p. 44°–48° C. The same compound was obtained using the method of Example 4.

EXAMPLE 6

4-Ethyl-4'-fluoro-2-hydroxybenzophenone-oxime.

4-Ethyl-4'-fluoro-2-hydroxybenzophenone (21.0 g, 80% pure) was treated with hydroxylamine hydrochloride (24.0 g) in a manner similar to that in Example 3, to give, after recrystallisation from benzene, the title compound as a white crystalline solid (10.7 g), m.p. 130°–2° C.

Microanalysis: $C_{15}H_{14}FNO_2$ requires 69.5% C, 5.4% H, 5.4% N, 7.3% F; found 69.2% C, 5.5% H, 5.2% N, 7.2% F.

EXAMPLE 7

2-Hydroxy-3-methyl-4'-chlorobenzophenone oxime

The ketone of Example 4 (7.5 g, 0.03 mole) in ethanol (18 ml.) was added with stirring to a solution of (85%) potassium hydroxide (20.74 g, 0.3 mole) in water (85 ml) at 10° C., this colloidal solution was treated with solid hydroxylamine hydrochloride (8.54 g, 0.12 mole) and stirred overnight. The solution was acidified with 5N HCl to give a solid, which was filtered, washed with water and stirred for 45 minutes, then treated with 5% Na₂CO₃ solution (30.5 ml), to remove unwanted oxime stereoisomer, filtered, washed with 5% Na₂CO₃ solution (100 ml) and then with water until free of alkali. The dried solid had m.p. 175°–177° C. Recrystallisation from 54% benzene-light petroleum (b.p. 60°–80° C.) mixture gave the oxime, m.p. 178° C. ("bonded isomer") 5.45 g.

found: C. 64.25; H. 4.79; Cl. 13.41; N. 5.3% $C_{14}H_{12}ClCO_2$ requires: C. 64.25; H. 4.6; Cl. 13.55; N. 5.35%

EXAMPLE 8

2-Hydroxy-3-methyl-4'-chlorobenzophenone oxime acetate.

Acetic anhydride (12 ml) was warmed to 60° C. and treated with the oxime of Example 7 (5.25 g, 0.02 mole). The stirred mixture was warmed to 80° C. to dissolve the oxime and the solution was then immediately cooled in an ice bath. The precipitated solid was filtered off, washed with light petroleum (b.p. 40°-60° C.) to give the acetate, 4.8 g, m.p. 154°-156° C.

found: C. 63.18; H. 4.86; Cl. 11.5; N. 4.77 $C_{16}H_{14}ClNO_3$ requires: C. 63.26; H. 4.64; Cl. 11.67; N. 4.6%

EXAMPLE 9

2-Hydroxy-3-ethylbenzophenone

This compound (44.67 g) was prepared from benzene (172 g, 2.2 mole) and 2-hydroxy-3-ethyl benzoic acid chloride (63.15 g, 0.34 mole), using the same conditions as in Example 4. The b.p. of the compound was 123°-126° C./0.14 mm, $\eta_D^{22}$ 1.6081, γ max. (film) 1630 cm$^{-1}$. The same compound was obtained using the method of Example 2.

EXAMPLE 10

2',4'-Dichloro-3-ethyl-2-hydroxybenzophenone

Aluminium chloride (26.7 g) was added in portions to a stirred mixture of 2-ethylphenol (12.2 g) and 2,4-dichlorobenzoyl chloride (23.1 g) in 1,1,2,2-tetrachloroethane (100 ml), and then the mixture was heated under reflux for 21 hours. On cooling, the solution was poured onto concentrated hydrochloric acid (100 ml) cooled with ice (200 g). The organic fraction was separated and combined with two further chloroform washings of the aqueous fraction, and then this was twice washed with 10% aqueous sodium carbonate solution, dried over magnesium sulphate monohydrate and evaporated to a dark viscous oil (30.0 g). This oil was distilled in vacuo, the first fraction (156°-172° C. at 0.06 mmHg) containing 85% of the required product. With ferric chloride solution a purple colour was obtained indicating the presence of an o-hydroxyketone). The ketone product was purified by chromatography on a silica column $\eta_D^{22}$ 1.6163. The same product was obtained using the method of Example 4.

EXAMPLE 11

4-Ethyl-3'-fluoro-2-hydroxybenzophenone

This compound was prepared from 3-ethylphenol (12.2 g), 3-fluorobenzoyl chloride (17.5 g) and aluminium chloride (26.7 g) in 1,1,2,2-tetrachloroethane (75 ml) using the same conditions as in Example 2, but heating under reflux, not at 105° C. The product was purified by chromatography on a silica column m.p. between 0° and 20° C. $\eta_o^{22}$ 1.5962. The same product was obtained using the method of Example 4.

EXAMPLE 12

4-Chlorobenzoylchloride (1.35 g, 0.0077 mole) was added dropwise to a solution of 4-ethylphenol (0.86 g, 0.0070 mole) in 2.5 N aqueous sodium hydroxide (5.6 ml). The mixture was shaken vigorously for 15 minutes when a light brown solid separated out. The mixture was diluted with water (10 ml) and the solid was filtered off, washed with water (3 × 20 ml), and dried. The solid was recrystallised twice from n-hexane to yield pale brown crystals of 4-ethylphenyl-4-chlorobenzoate, m.p. 66.5°-67° C.

The above ester (2.6 g) was heated with aluminium chloride (1.33 g) in tetrachloroethane for 6 hours at 125° C. A sample taken at the end of this time was added to dilute hydrochloric acid and the organic material was extracted into chloroform. Vapour phase chromatographic analysis of this solution detected no remaining ester, and comparison with an authentic sample showed the product to be 4'-chloro-5-ethyl-2-hydroxybenzophenone. Similarly prepared were:

5-Ethyl-2-hydroxy-4'-methylbenzophenone, m.p. 49°-51° C. and

4'-Chloro-3,5-diethyl-2-hydroxybenzophenone b.p. 188° C. at 1.4 mm/Hg.

EXAMPLE 13

2-Benzoyloxy-5-ethyl-4'-chlorobenzophenone

2-Hydroxy-5-ethyl-4'-chlorobenzophenone (5 g, 0.019 mole) was stirred vigorously in a solution of NaOH (7.5 g, 0.187 mole) in water (75 ml) and benzoyl chloride was added dropwise over 5 minutes. The temperature rose to around 50° C. The mixture was stirred for 1.5 hours at room temperature and was then extracted with ether, the ether washed with saturated NaCl solution, dried ($Na_2SO_4$), filtered and evaporated to leave the product, which was recrystallised from n-hexane to give white crystals of the desired product, m.p. 79°-81° C.

EXAMPLE 14

2-Acetoxy-4'-chloro-5-ethylbenzophenone

2-Hydroxy-5-ethyl-4'-chlorobenzophenone (3 g), in acetic anhydride (10 ml) and acetic acid (1 ml) were refluxed for 3.5 hours, and allowed to cool. The mixture was poured into dilute NaOH solution and extracted with chloroform. The chloroform was washed with 10% $NaHCO_3$ solution (50 ml), dried ($MgSO_4$) and evaporated to leave an oil which was distilled, b.p. 160°-165° C. at 3.5 mm/Hg (2.3 g) to give the desired product.

EXAMPLE 15

5-Ethyl-2-hydroxy-4'-trifluoromethyl benzophenone

Aluminium chloride (0.6 g, 0.004 mole) was stirred in dichloromethane (2 ml) and treated with 4-trifluoromethylbenzoyl chloride (1 g, 0.0048 mole) (ice-bath cooling) and then with 4-ethylanisole (0.6 g, 0.0044 mole) in dichloromethane (1 ml). The mixture was stirred at room temperature overnight and then poured into ice and concentrated hydrochloric acid and extracted with chloroform. The chloroform solution was washed with 10% $NaHCO_3$ solution (100 ml), dried ($MgSO_4$), filtered and evaporated to leave 5-ethyl-2-methoxy-4'-trifluoromethylbenzophenone (1.2 g) as a yellow oil. The latter was heated in 55% aqueous hydrogen bromide (27.5 ml) at 110°-120° C. for 5 hours. The mixture was evaporated to dryness to leave the required product.

EXAMPLE 16

5-Ethyl-2-hydroxy-3'-carboxy- and 3'-carbomethoxybenzophenone

Aluminium chloride (39.9 g, 0.3 mole) was stirred in dichloromethane (133 ml) and treated with 3-carbomethoxybenzoyl chloride (59.5 g, 0.3 mole) (ice-bath cooling), over 0.5 hours. 4-Ethylanisole (40.8 g, 0.3 mole) in dichloromethane (70 ml) was added to the stirred, cooled mixture, which was then stirred at room temperature overnight. The reaction mixture was processed as in Example 15 to leave 5-ethyl-2-methoxy-3'-carbomethoxybenzophenone. The latter was heated in 55% aqueous hydrogen bromide (500 ml) at 110°–120° C. for 5 hours. The mixture was evaporated to dryness to leave 5-ethyl-2-hydroxy-3'-carboxybenzophenone, which was characterised by having the correct C, H and N microanalysis. The latter carboxylic acid was then refluxed overnight in methanol (500 ml) containing concentrated sulphuric acid (5 ml), poured into water (1 L) and extracted with ether. The combined ethereal extracts were washed with saturated NaHCO$_3$ solution, dried (MgSO$_4$), filtered and evaporated to leave the desired ester, which gave a satisfactory microanalysis.

We claim:

1. A method of preventing asthmatic attacks in a mammal suffering from asthma comprising administering to said mammal a therapeutically effective dose of a compound sufficient to relieve the asthma of the formula:

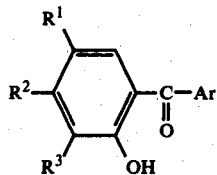

wherein R$^2$ is hydrogen or ethyl, R$^1$ and R$^3$ are hydrogen, methyl, or ethyl, at least one of R$^1$, R$^2$ and R$^3$ being other than hydrogen and Ar is a phenyl group optionally substituted by from one to three groups selected from chlorine, fluorine, methyl or trifluoromethyl.

2. Method as claimed in claim 1 wherein the compound 4'-chloro-5-ethyl-2-hydroxybenzophenone is administered.

3. Method according to claim 1 in which wherein one of R$^1$, R$^2$ and R$^3$ is ethyl, the others being hydrogen, and Ar is is phenyl, 4-chlorophenyl, 4-fluorophenyl, or 4-methylphenyl is administered.

* * * * *